US009867449B2

United States Patent
LaHood, Sr. et al.

(10) Patent No.: US 9,867,449 B2
(45) Date of Patent: Jan. 16, 2018

(54) SYSTEM AND METHOD OF MANUFACTURING A THREE-DIMENSIONAL COSMETIC PRODUCT

(71) Applicants: Richard Joseph LaHood, Sr., Washington, IL (US); Richard Joseph LaHood, Jr., Peoria, IL (US); John Paul LaHood, Washington, IL (US)

(72) Inventors: Richard Joseph LaHood, Sr., Washington, IL (US); Richard Joseph LaHood, Jr., Peoria, IL (US); John Paul LaHood, Washington, IL (US)

(*) Notice: Subject to any disclaimer, the term of this patent is extended or adjusted under 35 U.S.C. 154(b) by 216 days.

(21) Appl. No.: 14/745,328

(22) Filed: Jun. 19, 2015

(65) Prior Publication Data

US 2015/0366327 A1    Dec. 24, 2015

Related U.S. Application Data

(60) Provisional application No. 62/014,903, filed on Jun. 20, 2014.

(51) Int. Cl.
| | |
|---|---|
| *G06F 17/50* | (2006.01) |
| *A45D 40/30* | (2006.01) |
| *A45D 33/00* | (2006.01) |
| *B33Y 10/00* | (2015.01) |
| *B29C 64/165* | (2017.01) |
| *G06K 9/00* | (2006.01) |
| *B33Y 80/00* | (2015.01) |
| *A61M 35/00* | (2006.01) |

(52) U.S. Cl.
CPC ........... *A45D 40/30* (2013.01); *A45D 33/003* (2013.01); *B29C 64/165* (2017.08); *B33Y 10/00* (2014.12); *B33Y 80/00* (2014.12); *G06K 9/00281* (2013.01); *A61M 35/00* (2013.01)

(58) Field of Classification Search
CPC ... B29C 67/0081; B29C 64/165; G06F 17/50; G06K 9/00281
USPC ..................... 264/113; 382/118; 700/98, 119
See application file for complete search history.

(56) References Cited

U.S. PATENT DOCUMENTS

| | | | | |
|---|---|---|---|---|
| 5,934,343 A | * | 8/1999 | Gaylo ................. | B29C 67/0077 141/12 |
| 7,927,680 B2 | | 4/2011 | Marshall | |
| (Continued) | | | | |

OTHER PUBLICATIONS

Crook, Mink is a 3D Printer for Makeup, TechCrunch May 5, 2014.
3D Systems ChefJet Pro, iReviews Nov. 19, 2014.

*Primary Examiner* — Leo B Tentoni
(74) *Attorney, Agent, or Firm* — Katten Muchin Rosenman LLP

(57) ABSTRACT

A manufacturing process for three-dimensionally printing cosmetic products, and/or custom facial mask applicators using makeup powder as a fabrication medium. The process may use the versatile nature of makeup powder ingredients to stretch the usability of a makeup powder mixture across many platforms of facial cosmetics. The process may create custom, digital files that can be manufactured with high resolution, high complexity, and with a full spectrum of colors using Food and Drug Administration (FDA) compliant cosmetic grade dye. In particular, full-face makeup mask applicators that are based on an exact three-dimensional scan of the user's face.

21 Claims, 5 Drawing Sheets

Intermediate stage    Last layer printed    Finished part

(56) References Cited

U.S. PATENT DOCUMENTS

| | | | |
|---|---|---|---|
| 2001/0050031 A1* | 12/2001 | Bredt | B29C 67/0081 |
| | | | 106/162.9 |
| 2006/0013844 A1 | 1/2006 | Meriaux | |
| 2006/0098076 A1* | 5/2006 | Liang | A45D 44/005 |
| | | | 347/129 |
| 2008/0053476 A1 | 3/2008 | LaHood | |
| 2011/0234581 A1* | 9/2011 | Eikelis | G06K 9/00228 |
| | | | 345/419 |
| 2011/0284772 A1* | 11/2011 | Pugh | A61L 12/063 |
| | | | 250/492.1 |
| 2012/0329008 A1* | 12/2012 | Fishman | A61C 13/0004 |
| | | | 700/98 X |
| 2013/0169827 A1* | 7/2013 | Santos | G06K 9/00281 |
| | | | 348/207.1 |
| 2016/0068696 A1* | 3/2016 | Xu | B29C 67/0062 |
| | | | 428/451 |
| 2016/0332373 A1* | 11/2016 | Kuhn | B29C 67/0081 |

\* cited by examiner

SYSTEM AND METHOD OF MANUFACTURING A THREE-DIMENSIONAL COSMETIC PRODUCT

RELATED APPLICATIONS

This application claims priority to U.S. Provisional Patent Application No. 62/014,903 titled "Cosmetics Applicator System and Method" filed on Jun. 20, 2014, to which Applicant claims the benefit of the earlier filing and which is incorporated herein by reference in its entirety.

TECHNICAL FIELD

The present invention relates to cosmetics. More specifically, the present invention relates to a system and method of making a cosmetic applicator. Even more specifically, the present invention relates to a process of fabricating cosmetic products from a makeup powder using, for example, three-dimensional printing techniques.

BACKGROUND

Individuals who wear cosmetic materials often spend a considerable amount of time applying those cosmetic materials. In an attempt to save time in the application of the cosmetic materials, many cosmetic applicators have been developed. United States published patent application No. 2006/0013844 (the '844 application), Ser. No. 10/998,203, filed on Nov. 26, 2004, discloses such a cosmetic applicator for applying cosmetic materials to the face of an individual.

The cosmetic applicator disclosed in the '844 application includes a film layer having a first side and a second side. A cosmetic material is disposed on the first side of the film layer, and an adhesive layer is disposed on the second side of the film layer. The adhesive layer bonds the film layer to the face of the individual. The cosmetic applicator is shaped to fit different facial features of the face of the individual, e.g., an eye-shadow element is shaped to fit an eyelid of the individual. Additionally, the cosmetic material disposed on the film layer includes an appropriate composition and color for the respective facial feature onto which the cosmetic applicator is to be applied, e.g., the cosmetic material may include an appropriately colored eye shadow to the eyelid of the individual. A cover layer is disposed adjacent the adhesive layer to protect the adhesive layer before use. To apply the cosmetic material to the face of the individual, the release layer is removed, and the adhesive layer is applied to the appropriate facial feature of the individual, bonding the film layer and the cosmetic material disposed thereon onto the face of the individual. Accordingly, the cosmetic applicator adheres the film layer to the face of the individual, but does not transfer the cosmetic material to the face. This is not only uncomfortable, but does not permit the individual to blend the cosmetic material into the skin of the face surrounding the cosmetic applicator.

Cosmetic applicators for applying samples of cosmetic materials are also well known in the art. U.S. Pat. No. 5,980,960 (the '960 patent) Ser. No. 08/843,316 filed on Apr. 25, 1997, discloses such a sample cosmetic applicator. The cosmetic applicator of the '960 patent includes a backing layer defining a hole therethrough. A flexible layer is affixed to the backing layer and covers the hole. A cosmetic material is disposed on the flexible layer opposite the backing layer. A removable cover layer is disposed over the cosmetic material to protect the cosmetic material before use. The cosmetic material is applied by, removing the cover layer, inserting a finger through the hole to stretch the flexible layer outward, away from the backing layer, and then directly applying the cosmetic material to the appropriate facial feature on the individual's face, e.g., if the cosmetic material is a lip color, the cosmetic material is applied to the lips of the individual. This type of cosmetic applicator works well for individual applications of single cosmetic materials, but would require several different cosmetic applicators, one for each type of cosmetic material, to apply all of the different types of cosmetic materials utilized over the entire face of the individual.

Despite the prior attempts to improve facial makeup application, a need exists for a faster, more accurate, and more customizable way to create and apply makeup. Facial cosmetics have been applied in the same way for thousands of years. Furthermore, makeup ingredients are vastly similar across many platforms of makeup (e.g., blush, eye shadow, foundation, and concealer). The present invention facilitates the creation of custom-designed makeup products and, in particular, a makeup applicator mask that will apply precise, customized makeup in a fast, one-step application. The present invention may further employ a similar baseline of ingredients across the cosmetic industry.

SUMMARY OF THE INVENTION

The present invention is directed to cosmetics. More specifically, the present invention is directed to a system and method of making a cosmetic applicator or device. Even more specifically, the present invention is directed to a process of fabricating cosmetic products from a makeup powder using, for example, three-dimensional printing techniques.

According to a first aspect of the present invention, a method of manufacturing a makeup product for an individual may comprise: distributing a makeup powder layer on a powder bed within a print chamber, applying a first binder solution to at least a portion of said makeup powder layer to create a structural outer layer form, applying a second binder solution to at least a portion of said makeup powder to create a cosmetic inner layer, using a three-dimensional printing process. In certain aspects, the method may further comprise the step of generating a three-dimensional scan of the individual's face.

DESCRIPTION OF THE DRAWINGS

These and other advantages of the present invention will be readily understood with the reference to the following specifications and attached drawings wherein.

DETAILED DESCRIPTION

Preferred embodiments of the present invention will be described herein below with reference to the accompanying drawings. In the following description, well-known functions or constructions are not described in detail because they may obscure the invention in unnecessary detail. The present invention discloses a process of fabricating cosmetic products from a makeup powder using, for example, three-dimensional (3D) printing techniques. For this disclosure, the following terms and definitions shall apply:

The term "makeup powder," as used herein, generally refers to a cosmetic powder used to fabricate a cosmetic product, or portion thereof. The cosmetic powder may comprise, without limitation, one or more of the following: mica, titanium dioxide, acrylate copolymer, acrylic polymers, polyvinyl alcohol, polyvinylpyrrolidone, hydrolyzed collagen protein, magnesium oxide, maltodextrin, arrowroot starch, bismuth oxychloride, kaolin, cellulose, aluminum sulfate, silicone elastomer powder, aloe vera, calcium carbonate, talc, magnesium myristate, magnesium stearate, tapioca starch, zinc oxide, silica and silicone microspheres. The makeup powder may be, for example, a neutral color (e.g., clear or white) and configured to receive one or more dyes, ink, and/or additives (e.g., antibiotics, medications, hypoallergenic ingredients, etc.).

The term "binder," or "binding agent" as used herein refers to a liquid or solution that is passed through a print head and selectively joins layers to fabricate a cosmetic product, or portion thereof. The binder may comprise, without limitation, one or more of the following: water, ethanol, isopropyl alcohol, FD&C grade dye, D&C grade dye, natural dyes, triglycerides, mineral oil, vitamin E oil, emulsifiers, surfactants, wetting agents, structural proteins, triethanolamine and sulfosuccinate. The term "outer layer binder" as used herein refers to the binder used to fabricate the structural outer layer form 1, or "Layer O." The term "inner layer binder" as used herein refers to the binder used to fabricate the cosmetic inner layer 2, or the "Layer I." The outer layer binder and inner layer binder may have distinct compositions, such that for any makeup product manufactured using the invention, at least one structural outer layer form is created adjacent to at least one cosmetic inner layer.

Figure 1:
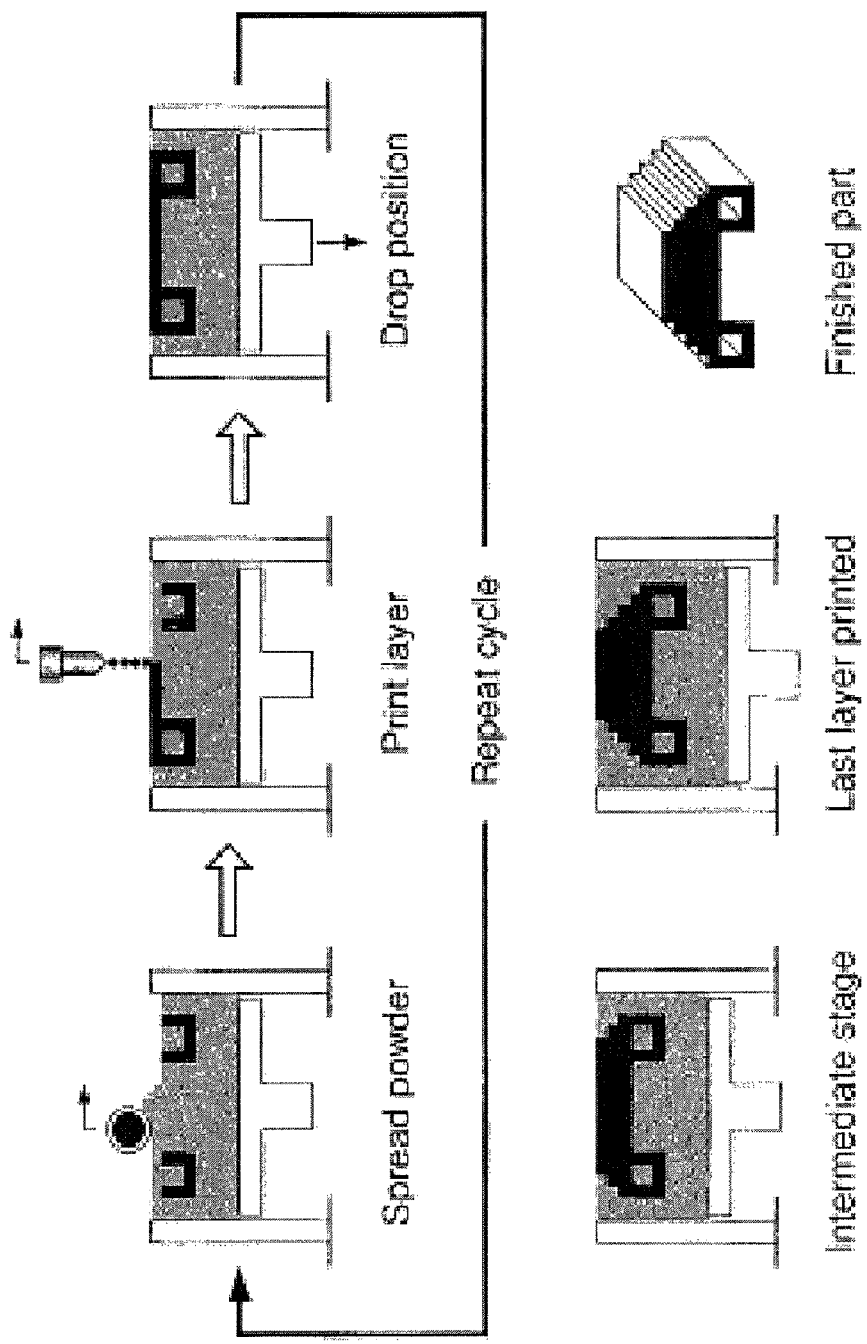
FIG. 1 illustrates an example three-dimensional printing (3DP) process.

The term "three-dimensional printing" or "3DP," as used herein, generally refers to a manufacturing technique for fabricating a three-dimensional object or material. An example 3DP technique may function by building an object or material in layers from, for instance, a computer model of the desired object or material, as seen in FIG. 1. A slicing algorithm may draw detailed information for every layer.

One aspect of the present invention relates to the process of printing custom, whole-face cosmetic masks and other custom makeup products from a makeup powder using one or more 3DP techniques. More specifically, the present invention relates to fabricating custom makeup products ranging from custom applicators to compartmentalized color palettes in a makeup powder bed, layer by layer, using one or more 3D printing techniques, such as 3DP (also known as "binder jetting" or "drop-on powder"). The process disclosed herein may further be employed for medical applications. For example, a mask may be fabricated with a region adapted to make contact with a lesion, wherein the mask applies a medication to said lesion region.

Figure 4:
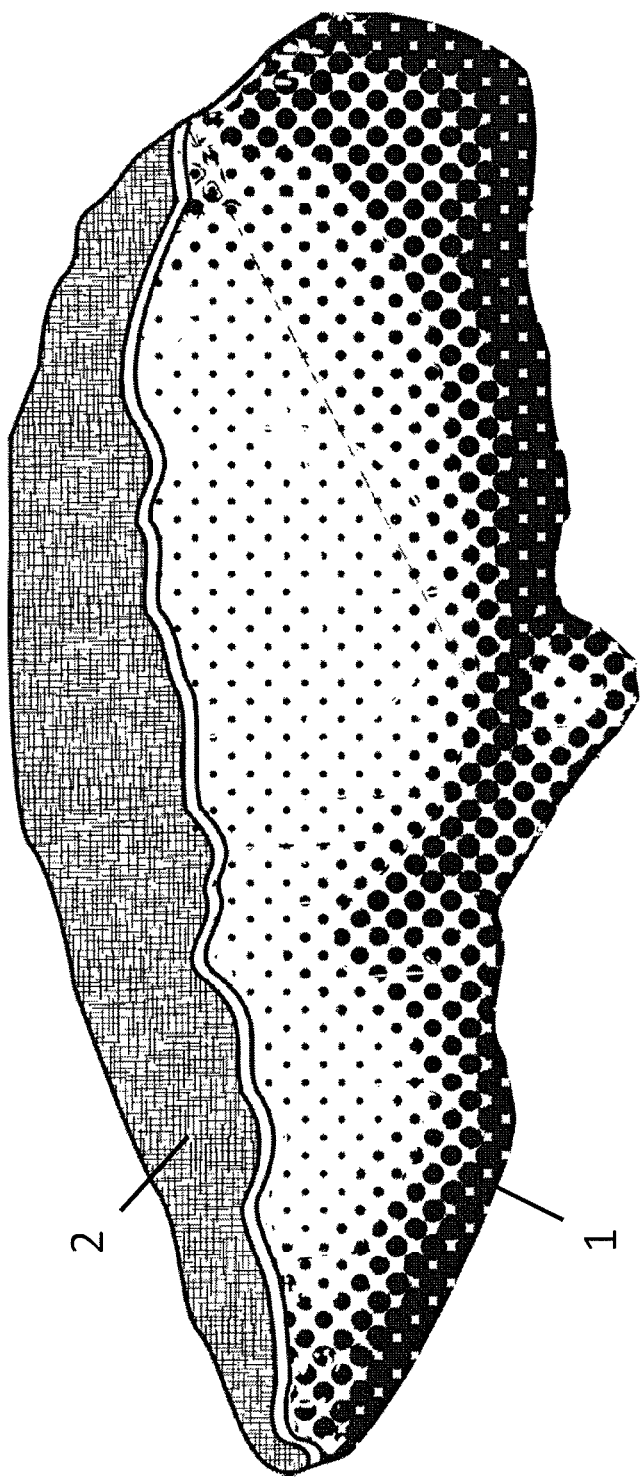
FIG. 4 illustrates the composition of a mask made using the claimed method with a structural outer layer and a cosmetic inner layer.
Figure 5:
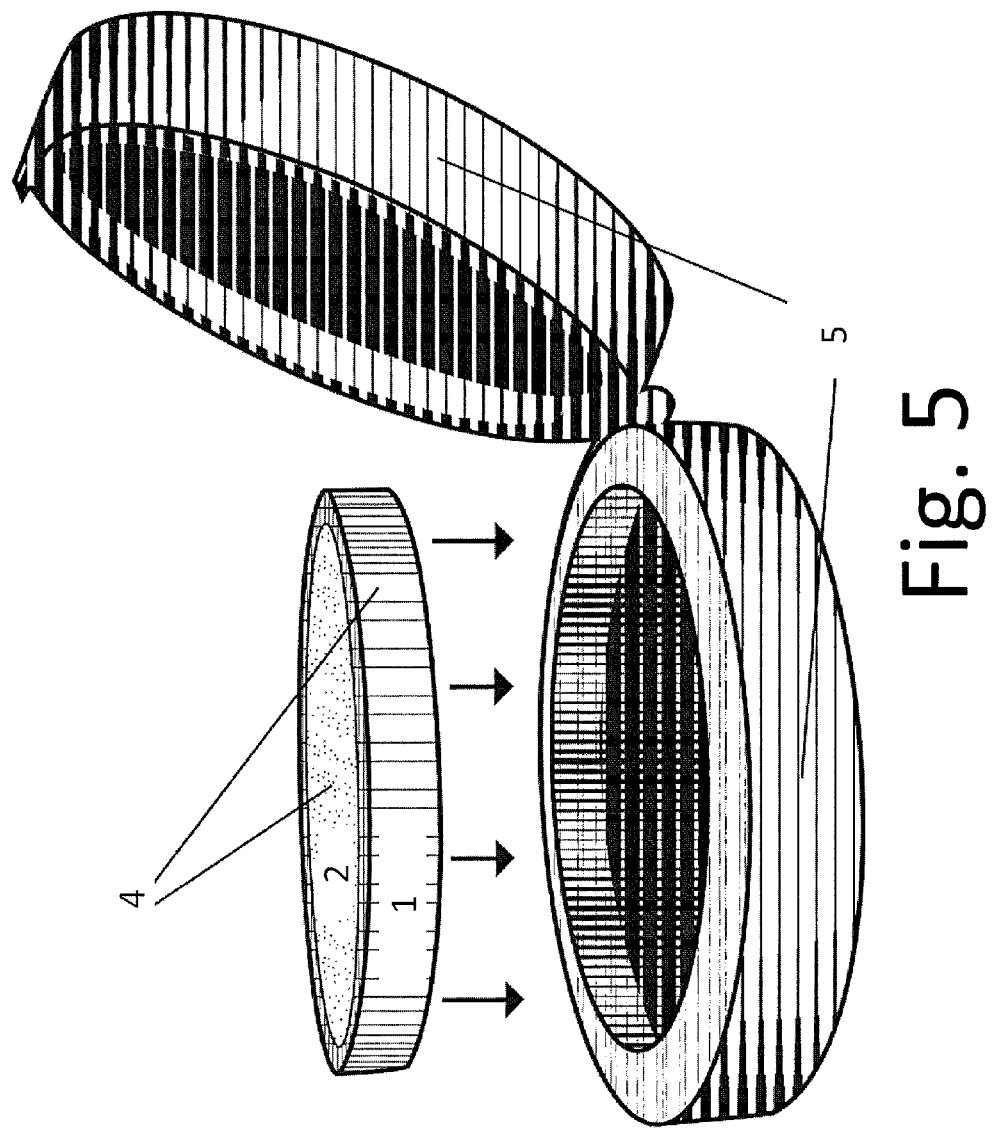
FIG. 5 illustrates a 3D printed cosmetic insert made using the claimed method having a structural outer layer and a cosmetic inner layer, being placed in pre-manufactured case.

With reference to FIG. 1, during a 3DP process, an inkjet print head, for example, traverses a bed of makeup powder, selectively depositing a binding agent (e.g., in a liquid form). Additional colored print heads may (e.g., simultaneously) deposit cosmetic grade dye to adjacent sections, or in some cases the same sections of each layer. Alternatively, cosmetic grade dye is integrated into the binder itself. The binding agents will each solidify the makeup powder to different strengths. The outer layer binder is used to solidify the makeup powder into the structural component of the printed object. This section of the object is called the "O layer." The inner layer binder, which may comprises cosmetic dye, is used to more loosely solidify the powder within the "I layer" section of the print. This process may use inner layer binders in four different colors (cyan, magenta, yellow and black) and may use these four color binders to achieve virtually any color within the printed object. The process of using these colors to create any color is called "CMYK color." Other color combinations, such as Red-Blue-Green ("RBG") or Pantone®Hexachrome, may also be used. Additional inner layer binder without dye may be used to alter the saturation, translucency, or other visual characteristics of the cosmetic inner layer. For example, as will be discussed with regard to FIGS. 2 and 4, the outer layer binder may be used to harden Layer O 1 to give rigidity, while the inner layer binder may be used to more loosely solidify the powder within Layer I 2. A thin layer of additional makeup powder may then be spread on top of the completed section, whereby the process is repeated with each subsequent layer adhering to the preceding layer. For example, a piston that supports the powder bed and the part in progress may lower so that the next powder layer can be spread and selectively joined. When the cosmetic component is complete, any unbound makeup powder may be automatically and/or manually removed in a process called "de-powdering." The unbound makeup may be reused in later printing processes. The de-powdered part (i.e., the cosmetic component, which may be a mask) may further be subjected to one or more infiltrates (or other treatments) to yield properties desired in the final part. Thus, using a 3DP process, the printer can solidify and/or color a plurality of layers to manufacture custom makeup products from makeup powder.

Because the 3DP process can color each layer (or portion thereof), it is possible to employ a single makeup powder that may be customized to provide a particular color, group of colors, and/or pattern. Different powder and binder recipes may be used in separate prints depending on the desired end product. For example, a cosmetic mask may use a different combination of makeup powders and binders than the combination of makeup powders and binders intended for printing cosmetic pallets or cases. Employing a single makeup powder is advantageous in that it reduces cost and enables the printer to employ a single powder reservoir, rather than a powder reservoir for each color. Moreover, mixing binders to color a single makeup powder provides for a greater array of shades of color.

The 3DP process may be used to print cosmetic products from, for example, computer-aided design (CAD) models that may be either three-dimensionally scanned, created using 3D design software, or downloaded from a digital database. For example, according to a first aspect, this cosmetic printing process may start with the user employing a 3D scanner to map (e.g., generate) a model of the user's facial structures, or a portion thereof. That is, the scan can provide a precise digital representation of the size, contour, colors, and shape of the individual's face in the form of facial model data. Example suitable 3D scanning techniques for digitally acquiring the shape of a face in connection with the present cosmetic printing process include, without limitation, contact and non-contact (e.g., active scanners and passive scanners) 3D scanners. Contact 3D scanners function by probing the subject (e.g., the face) through physical touch. Because a human face may not rest stably on a flat surface, the head may be supported and/or held firmly in place by a fixture. An example contact 3D scanner includes a coordinate measuring machine. Conversely, a non-contact active scanner, for example, operates by emitting a form of radiation (or light) and detecting its reflection or radiation passing through object in order to probe an object or environment. Possible types of emissions used include light, ultrasound, or x-ray. For example, triangulation-based 3D laser scanners are active scanners that use laser light to probe the environment. Triangulation range finders have a limited range of some meters, but their accuracy is relatively high. The accuracy of triangulation-based scanners is highly accurate and on the order of tens of micrometers.

Because scanning the user's face will likely be performed at home or on the go, a hand-held scanner (e.g., using a laser medium) may be used to generate facial model data through a triangulation mechanism. For instance, a laser dot or line may be projected onto the user's face from a hand-held device (which may be embodied within a portable device, such as a smart phone) and a sensor (typically a charge-coupled device or position-sensitive device) that measures the distance to the surface. Data is collected in relation to an internal coordinate system and therefore, to collect data when the scanner is in motion, the position of the scanner must be determined. The position can be determined by the scanner using reference features on the surface being scanned (typically adhesive reflective tabs, but natural features may also be used) or by using an external tracking method. External tracking often takes the form of a laser tracker (to provide the sensor position) with an integrated camera (to determine the orientation of the scanner) or a photogrammetric solution using three or more cameras providing the complete six degrees of freedom of the scanner.

This manufacturing process may potentially use another 3D printing process called SLS, or Selective Laser Sintering. This process would utilize a Laser to solidify or sinter the outer, structural layer instead of the liquid binder. The cosmetic inner layer would still be solidified using a liquid binder. The rest of the process is similar to the 3DP process where in the makeup powder is spread in a powder bed and subsequently built up layer by layer.

Prior to commencing the cosmetic printing process, because the facial model data may be unique to the specific user, a user may first be instructed to prepare, or otherwise provide, his or her facial model data. The facial model data may be manipulated via computer and may be further cropped from a head to a face region (or it can be manually edited into a face in any 3D design software). For example, the cosmetic printing process may employ 3D design software to create or manipulate the facial model data, which may be used to print a custom cosmetics product. Examples of such 3D design software include, without limitation, Rhinoceros 3D®, Sketch up®, SolidWorks®, MeshLab, Cheetah3D and Adobe Photoshop®. The scan may also include color information about the users face. In addition to the scale and dimension information, the scanner may also provide the exact color and tone of the users skin, lips and eyes. The 3D design software may be used to identify a facial feature of interest that should be addressed by the cosmetic product. For example, if a region having an imperfection (e.g., a scar, birthmark, etc.) is detected, the 3D design software may mask the imperfection by generating a cosmetic product having a specific color or thickness to mask that specific region.

During the cosmetic product design stage, the facial model data may be imported into the 3D design program and displayed on a computer terminal (which may be a portable device, such as a smart phone or tablet computer) as a representation of the user's face, such that color can be manipulated by the user through a computer terminal. For example, the face can be digitally painted with color on screen. Colors may be selected from a predetermined pallet of colors, or a color picker. The selected color may then be used to paint the user's face, or portion thereof, in the desired color or colors. In certain aspects, predetermined makeup colorings and/or patterns (e.g., layouts) may be selected from a database and applied to the specific facial model data.

This digital onscreen representation enables the user to accurately visualize different makeup colorings and/or patterns on their face (e.g., highlighting and contouring). The digital interface will also allow the user to paint highly precise, symmetrical makeup lines and color variations. A trained professional in a commercial setting may be employed during this step of the process; however, the step may alternatively be done by the user (e.g., at home). Sections of the onscreen facial representation may be colored based on the makeup color preferences of that user or the recommendations of the trained professional. For example, the eyelids of the face may be painted the color of that person's desired eye shadow. Additionally all of the color compositions will correspond appropriately to the facial feature they are representing. Daily-use makeup designs are a possible application for this process; however it may also be used for theatrical makeup, Halloween makeup, sporting event makeup (e.g., face paint for a particular team), and hunting/military camouflage.

Once the color design is complete, prior to printing, the face may be inverted into a mask. This may be accomplished via the computer, or by inverting the convex facial scan into a concave facial mask. At this time sections of the mask may be removed to allow it to fit more comfortably, specifically the area around the nostrils and the mouth. Removing these sections will allow the user to breath while the mask is pressed to the user's face. The user may also opt to remove small slits around the eyes to allow the eyelashes to egress.

Figure 2:
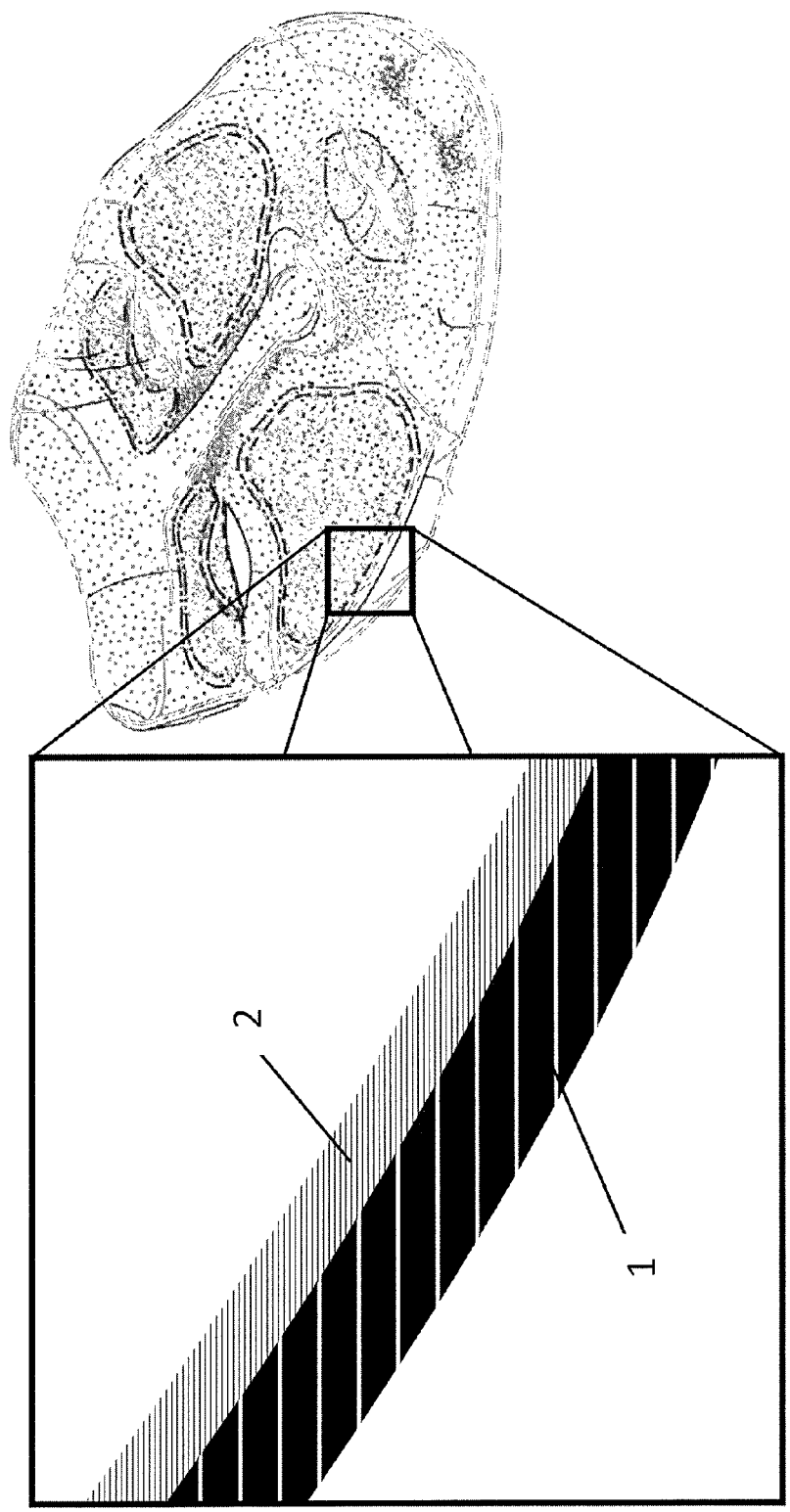
FIG. 2 illustrates a mask made using the claimed method having a structural outer layer and a cosmetic inner layer.

With reference to FIG. 2, the concave facial mask may be assigned two layers through its thickness, which may be, collectively, for example, 1,000 to 12,000 microns thick. The outer layer (layer O) 1 is responsible for giving the mask rigidity and strength, while the inner layer (layer I) 2 is responsible for the color that was previously "painted" via the design stage. Additional information regarding a suitable mask and components thereof may be gleaned from commonly owned U.S. Ser. No. 11/468,018 to Richard LaHood, Sr. and Richard LaHood, Jr., entitled "Cosmetics Applicator," which was filed on Aug. 29, 2006, and published as US20080053476 A1. However, while U.S. Ser. No. 11/468, 018 employs a plurality of different cosmetic materials, the present disclosure overcomes this need by enabling a user to fabricate a comparable mask using only a single makeup powder via, for example, a 3DP process as disclosed herein.

Once the makeup product is ready to be fabricated (e.g., colors chosen, and/or customized; and overall shape and size is determined), the cosmetic printing process may use the 3DP process to fabricate the masks from the makeup powder as its medium. Each layer begins with a thin distribution of powder spread over the surface of a powder bed. The process then uses inkjet style print heads to harden only the desired sections of each layer. The primary print head will use a binding agent to harden the powder on the outside layer (layer O) 1 of each mask to give structure and rigidity. Simultaneously, a second color print head will more loosely solidify and pigment the inner layer (layer I) 2 of the mask using the inner binder. These steps repeat over and over until the process is complete. This will result in a custom makeup product with a rigid outer layer 1, lined on the inside with a cosmetic inner layer 2 adhered to the structural outer layer 1 (that is also comprised of makeup powder).

The makeup powder may comprise, without limitation, one or more of the following: mica, titanium dioxide, acrylate copolymer, acrylic polymers, polyvinyl alcohol, polyvinylpyrrolidone, hydrolyzed collagen protein, magnesium oxide, maltodextrin, arrowroot starch, bismuth oxychloride, kaolin, cellulose, aluminum sulfate, silicone elastomer powder, aloe vera, calcium carbonate, talc, magnesium myristate, magnesium stearate, tapioca starch, zinc oxide, silica and silicone microspheres. In one embodiment of the invention, the makeup powder comprises between about 10% and about 70% mica by volume, preferably between about 30% and about 50% mica by volume, and more preferably about 40% mica by volume. In another embodiment, the makeup powder comprises about 10% to about 50% titanium dioxide by volume, preferably about 25% to about 35% titanium dioxide by volume, and more preferably about 30% titanium dioxide by volume. In another embodiment, the makeup powder comprises about 10% to about 50% acrylate copolymer by volume, preferably about 25% to about 35% acrylate copolymer by volume, and more preferably about 30% acrylate copolymer by volume. In one embodiment of the invention, the makeup powder comprises hypoallergenic ingredients.

The binders may comprise, without limitation, water, ethanol, isopropyl alcohol, FD&C grade dye, D&C grade dye, natural dyes, triglycerides, mineral oil, vitamin E oil, emulsifiers, surfactants, wetting agents, structural proteins, triethanolamine and sulfosuccinate. In one embodiment of the invention, the outer layer binder comprises about 1% to about 20% triethanolamine by volume, preferably about 5% to 15% triethanolamine by volume, and more preferably about 10% triethanolamine by volume. In one embodiment of the invention, the inner layer binder comprises about 5% and about 35% sulfosuccinate by volume, preferably between about 15% and about 25% sulfosuccinate by volume, and more preferably about 20% sulfosuccinate by volume. In one embodiment of the invention, the inner layer binder comprises about 1% to about 20% botanical alpha-hydroxy acid by volume, preferably about 5% to 15% botanical alpha-hydroxy acid by volume, and more preferably about 10% botanical alpha-hydroxy acid by volume. In one embodiment of the invention, the binders comprise hypoallergenic ingredients.

Once the print job is complete, excess makeup powder may be removed from the print bed and recycled for the next print job. In one embodiment, a custom makeup mask is left, that can be imprinted on the user's face for a one-step makeup application. Layer O 1 will stay intact, while layer I 2 will transfer onto the user upon contact with the user's face. The mask is then removed from the face of the user, leaving the cosmetic materials disposed thereon. The mask may require a conditioning spray to coat Layer I to help the makeup transfer. The final result will allow an individual to apply all of their desired cosmetics to their entire face with a single, simple, and convenient cosmetic applicator, thereby reducing the overall time it takes the individual to apply a full makeup composition to their face. The mask may be designed as a one-time-use disposable applicator, or could be designed for multiple uses.

This manufacturing process may be capable of fabricating a plurality of masks at a given time (e.g., standing up vertically or horizontally within the print chamber). It will also make a well-designed makeup mask highly repeatable with consistent results. Depending on the size of the print bed, this process could potentially print hundreds of masks in a single batch. The natural shape of the masks will allow them to be lined up very close to each other with thin "gaps" of unsolidified makeup powder in between. This will allow for maximum efficiency in each batch of prints. Furthermore, this technology will allow for very high print resolution making highly complicated color blending and color designs simple to execute.

Figure 3:
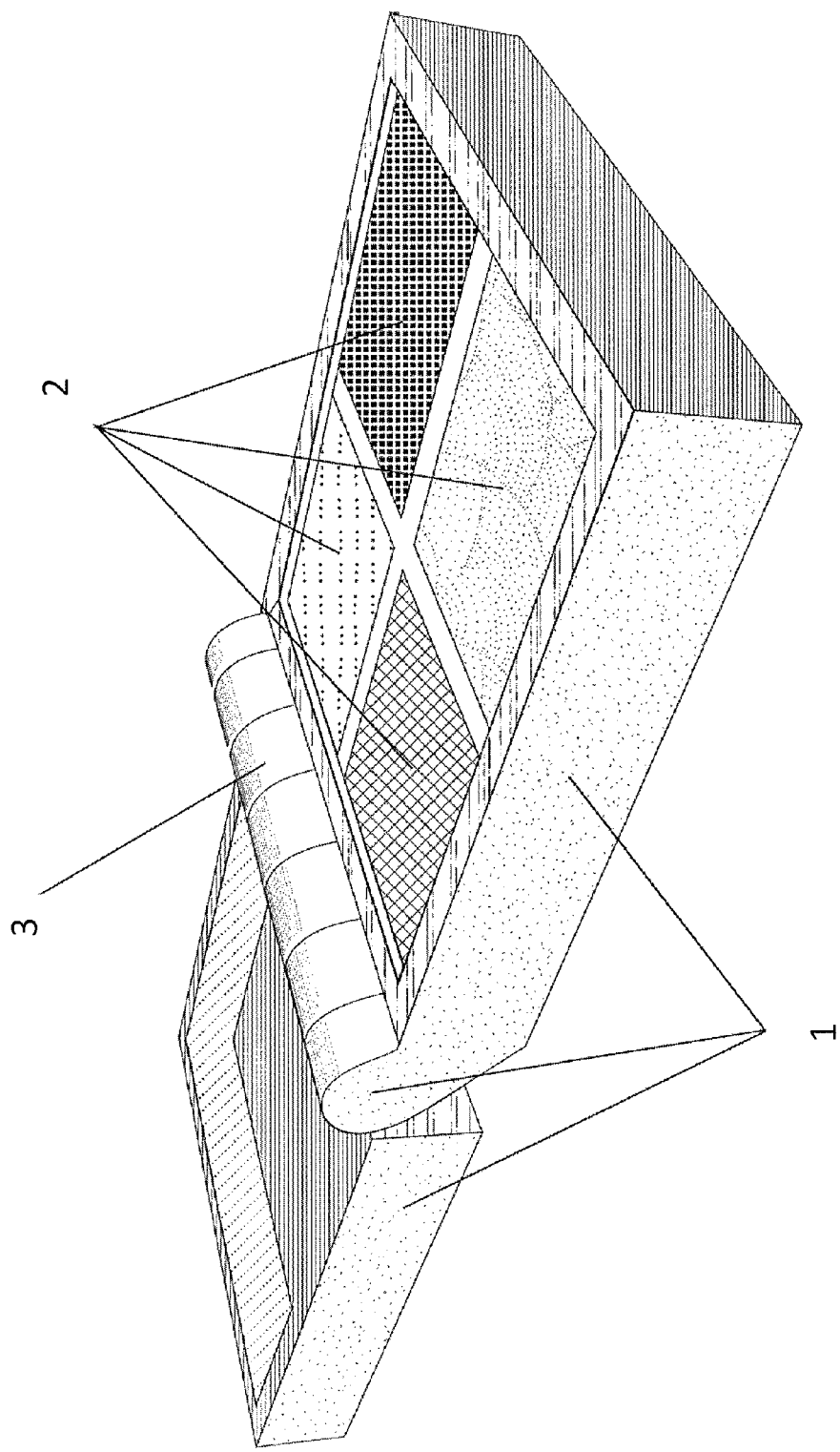
FIG. 3 illustrates a makeup case made using the claimed method having a structural outer layer, a cosmetic inner layer, and an articulated hinge.

With reference to FIG. 3, aside from makeup masks, this process will also be used for manufacturing custom, makeup-related CAD models into makeup accessories. It will use the claimed manufacturing process to print various makeup products, such as compartmentalized color palettes to personalized compact case devices with custom colors. Digital color maps displaying all available printable colors may assist a user in choosing which color makeup products to print. This digital color may automatically suggest colors, or automatically limit the colors to choose based on various inputs. For instance, the color map could be limited based on pre-selected colors by a certain stylist or artist.

Additionally, algorithms created by independent programmers, stylists or artists could automatically generate color schemes to compliment an individual's skin tone, hair color, clothes, or accessories. To assist in limiting the color map, an individual may upload a digital image of the face or outfit to generate limited color selections. When combined with an at-home or locally available three-dimensional printer utilizing the present invention, an individual would have access to on-demand printing of thousands of colors to rapidly compliment a look or style. Because this type of printing can produce interlocking moving parts, it will be possible to print things like compact makeup cases with hinged lids 3. It may print other moving mechanisms, such as lipstick that twists out of a structural case. Theses printed cosmetic products may also be designed with limited structure (O Layer) around them and be simply designed to be inserted 4 into a standard case or housing package 5 that may be manufactured away using other techniques.

The above-cited patents and patent publications are hereby incorporated by reference in their entirety. Although various embodiments have been described with reference to a particular arrangement of parts, features, and the like, these are not intended to exhaust all possible arrangements or features, and indeed many other embodiments, modifications, and variations will be ascertainable to those of skill in the art. Thus, it is to be understood that the invention may therefore be practiced otherwise than as specifically described above.

What is claimed is:

1. A method of manufacturing a makeup product using a three dimensional printing process, the method comprising:
   selecting, through a digital interface, a three-dimensional digital model comprising a cosmetic form and a structural form adjacent to the cosmetic form;
   selecting one or more colors from a digital color map within the digital interface for at least part of the cosmetic form of the three-dimensional digital composition model; and
   depositing multiple makeup powder layers on a powder bed within a print chamber to create at least one cosmetic compositional three-dimensional object, the cosmetic compositional three-dimensional object comprising:

a structural outer layer solidified using an outer layer binder deposited through a first print head in accordance with the structural form of the three-dimensional digital model, and at least one consumable color cosmetic inner layer formed using an inner layer binder deposited through a second print head in accordance with the cosmetic form of the three-dimensional digital model, wherein the at least one consumable color cosmetic inner layer is adjacent to the structural outer layer, and wherein the inner layer binder comprises a cosmetic colorant.

2. The method of claim 1, wherein the cosmetic compositional three-dimensional object is a cosmetic applicator mask.

3. The method of claim 2, wherein the cosmetic form of the three-dimensional digital model is modeled from a three-dimensional scan of an individual's face.

4. The method of claim 2, wherein the cosmetic form of the three-dimensional digital model is modeled using three-dimensional design software.

5. The method of claim 2, wherein the cosmetic form of the three-dimensional digital model is modeled after a design downloaded from an online database.

6. The method of claim 1, wherein the structural outer layer is an articulated makeup compact.

7. The method of claim 1, wherein the cosmetic colorant is a cosmetic grade dye.

8. The method of claim 7, wherein the cosmetic grade dye comprises a mixture of at least two of cyan, magenta, yellow, or black dye that matches a color of the one or more colors selected from the digital color map.

9. The method of claim 1, wherein the cosmetic colorant is a cosmetic pigment.

10. The method of claim 1, wherein the structural outer layer is solidified using a laser.

11. The method of claim 1, wherein the inner layer binder comprises about 20% sulfosuccinate and about 10% botanical alpha-hydroxy acid by volume.

12. A method of manufacturing a makeup product using a three dimensional printing process, the method comprising:

scanning an individual's face using a three-dimensional scanner and generating a three-dimensional digital rendering;

digitally applying a cosmetic design to the three-dimensional digital rendering generated from the individual's face;

inverting the three-dimensional digital rendering to create a three-dimensional digital model for a cosmetic mask applicator having a dimensional shape of the users face, the three-dimensional digital model comprising a structural outer form adjacent to a color cosmetic form;

removing at least one section of the three-dimensional digital model to improve a fit of the cosmetic mask applicator; and depositing multiple makeup powder layers on a powder bed within a print chamber to create the cosmetic mask applicator, the cosmetic mask applicator comprising:

a structural outer layer solidified using an outer layer binder deposited through a first print head in accordance with the structural form of the three-dimensional digital model, and at least one consumable cosmetic inner layer formed using an inner layer binder deposited through a second print head in accordance with the cosmetic form of the three-dimensional digital model, wherein the at least one consumable color cosmetic inner layer is adjacent to the structural outer layer, and wherein the inner layer binder comprises a cosmetic colorant.

13. The method of claim 12, wherein the cosmetic colorant is a cosmetic pigment.

14. The method of claim 12, wherein the cosmetic colorant is a cosmetic grade dye.

15. The method of claim 12, wherein the inner layer binder further comprises a medicated ointment.

16. A method of manufacturing a makeup product using a three-dimensional printing process, the method comprising:

capturing color information data of an individual's face;

selecting, through a digital interface, a three-dimensional digital model comprising a cosmetic form and a structural form adjacent to the cosmetic form;

selecting one or more colors from a digital color map based on the color information data of the individual's face for at least part of the cosmetic form of the three-dimensional digital composition model; and depositing multiple makeup powder layers on a powder bed within a print chamber to create a cosmetic compositional three-dimensional object, the cosmetic compositional three-dimensional object comprising:

a structural outer layer solidified using an outer layer binder deposited through a first print head in accordance with the structural form of the three-dimensional digital model, and at least one consumable cosmetic inner layer formed using an inner layer binder deposited through a second print head in accordance with the cosmetic form of the three-dimensional digital model, wherein the at least one consumable color cosmetic inner layer is adjacent to the structural outer layer, and wherein the inner layer binder comprises a cosmetic colorant.

17. The method of claim 16, wherein the cosmetic colorant is cosmetic grade dye comprising at least two of cyan, magenta, yellow, or black dye to match a color of the one or more colors selected from the digital color map.

18. The method of claim 16, wherein the cosmetic colorant is cosmetic pigment.

19. The method of claim 16, wherein the outer layer form is an insert for an existing case.

20. The method of claim 16, wherein the inner layer binder comprises a cosmetic wetting agent.

21. The method of claim 16, wherein the structural outer layer form is solidified using a laser.

* * * * *